United States Patent [19]

Heilman, Jr.

[11] Patent Number: 4,659,568

[45] Date of Patent: Apr. 21, 1987

[54] PROCESS FOR SOLUBILIZATION, PURIFICATION AND CHARACTERIZATION OF PROTEIN FROM INSOLUBLE PROTEIN AGGREGATES OR COMPLEXES AND COMPOSITIONS OF MATTER THEREFROM

[75] Inventor: Conrad J. Heilman, Jr., Chester, N.Y.

[73] Assignee: American Cyanamid Company, Stamford, Conn.

[21] Appl. No.: 706,533

[22] Filed: Feb. 27, 1985

[51] Int. Cl.$^4$ .......................... C07K 3/28; C07K 3/14; C07K 3/18; C07K 3/20
[52] U.S. Cl. .................................. 424/88; 530/395; 530/415; 530/417; 530/423; 530/825; 530/826; 530/419; 530/809; 424/89; 424/92; 435/68; 435/172.2; 435/172.3; 435/240; 435/241
[58] Field of Search ...................... 260/112 B, 112 R; 424/88, 89, 92; 435/68, 172.2, 172.3, 240, 241

[56] References Cited

U.S. PATENT DOCUMENTS 3,519,400  7/1970  Anderson ................... 260/112 R X
3,838,144  9/1974  Leach ............................. 260/112 R

OTHER PUBLICATIONS

Hilleman, M. R., et al., *Journal of Infection*, 7, Supp. 1, 3 (1983).
Dernick, R., "Antigenic Structure of Poliovirus", *Developments in Biological Standardization*, 47, 319 (S. Karger, Basel, 1981).
Tabor, E., et al., *Journal of Medical Virology* (U.S.A.), 11, 1 (1983).
Schlecht, S. and Bhatnagar, N., *Zentral Bakteriol Mikrobial Hyg.* (Germany, West), 251(2), 196 (1981).
Lehrer, S. B., et al., *Journal of Immunology* (U.S.A.), 114(1), 34 (1975).
Dalen, A. B., *Acta Path. Microbiol. Scan.*, Section B (Denmark), 561 (1975).
Helting, T. B. and Blackkolb, F., "An Effective Procedure for Preparing Extracted Protected Antigen from *Bordetella pertussis*", in *Third International Symposium on Pertussis*, National Institutes of Health, Part 6, pp. 331–337 (1978).
Kita, E., et al., *Microb. Immunol.*, 27, 7 (1983).
Kew, O. M., et al., *Journal of Virology*, 33, 256 (1980).
Helting, T. B. and Blackkolb, F., *Acta. Path. Microbiol. Scan.*, Section B, 89, 93 (1981).
Freedman, M., et al., *Journal of Immunological Methods*, 6, 165 (1974).
O'Brien, A. D., et al., *Infection and Immunity*, 30, 170 (1980).
Goch, H., et al., *Archivum Immunologiae et Therapiae Experimentalis*, 24, 349 (1976).
Mekalanos, J. J., et al., *Infection and Immunity*, 20, 552 (1978).

*Primary Examiner*—Howard E. Schain
*Attorney, Agent, or Firm*—Gregg C. Benson

[57] ABSTRACT

This invention discloses a novel process for the solubilization, purification and characterization of a protein or proteins from insoluble protein aggregates or complexes. The novel process comprises the use of a dissociating step gradient which can be followed by further purification and concentration. Also disclosed are compositions of matter and vaccines comprising one or more proteins purified according to the novel process of this invention.

20 Claims, 2 Drawing Figures

PROCESS FOR SOLUBILIZATION, PURIFICATION AND CHARACTERIZATION OF PROTEIN FROM INSOLUBLE PROTEIN AGGREGATES OR COMPLEXES AND COMPOSITIONS OF MATTER THEREFROM

BACKGROUND OF THE INVENTION

1. Field of the Invention

This invention relates generally to a purification process for proteins which are present in insoluble complexes or aggregates. In particular, this invention concerns the use of a dissociating concentration step gradient such as an urea concentration gradient to selectively solubilize and separate proteins in complexes or aggregates as well as characterize said proteins. In addition, this invention concerns compositions of matter comprising one or more proteins which have been solubilized and purified from insoluble protein aggregates according to the process of this invention. While examples of the invention contained herein concern the purification of recombinant Herpes simplex virus Type 1 glycoprotein D (HSV gD-1), the invention is not limited thereto but concerns the solubilization and purification of proteins from insoluble protein complexes or aggregates in general as well as compositions of matter derived therefrom. Furthermore, for the purposes of this invention, protein aggregates are to include and be considered the same as protein complexes.

DESCRIPTION OF THE PRIOR ART

With the advent of recombinant DNA technology has come the promise of producing through microbial systems, among other things, proteins in commercially significant quantities which heretofore were impossible and/or cost prohibitive to produce. As a result, numerous laboratories are employing recombinant DNA technology to produce expression vectors capable of directing the synthesis of specific human, bacterial, viral or other proteins. Very often, these recombinant DNA derived proteins form insoluble aggregates in the host microbial system. [Harris, T. J. R., "Expression of eukaryotic genes in *E. coli*", in *Genetic Engineering*, Vol. 4, Williamson, R., (Ed.), (Academic Press, London, U.K.), pp 127-183; Williams, D. C., et al., *Science*, 215, 687 (1982); Cheng, Y-S. E., *Biochemical and Biophysical Research Communications*, 111, 104 (1983); and Wetzel, R. and Goeddel, D. V., "Synthesis of polypeptides by recombinant DNA methods", in *The Peptides*, Vol. 5 (Academic Press, Inc., 1983) pp 1-64.]

In addition to protein aggregates which result from the use of recombinant DNA expression vectors, there are naturally occurring aggregate protein complexes common to numerous biological systems. [Scopes, R. K., "Separation of Precipitates and Particulate Material", in *Protein Purification Principles and Practice*, Cantor, C. R., (Ed.), (Springer Advanced Texts in Chemistry, 1982) pp 3-8.]

Thus, recovery and purification of a specific protein or specific proteins which are part of such aggregates was a common and substantial problem faced by those practicing in the art. The production of vaccines and other compositions of matter comprising one or more proteins which existed as insoluble aggregates was also a significant problem.

The use of urea to inactivate pathogens has been described. [Hilleman, M. R., et al., *Journal of Infection*, 7, Supp. 1, 3 (1983); Dernick, R., "Antigenic structure of poliovirus", International Symposium on Reassessment of Inactivated Poliomyelitis Vaccine, Bilthoven, 1980, *Developments in Biological Standardization*, 47, 319, (S, Karger, Basel, 1981); and Tabor, E., et al., *Journal of Medical Virology* (U.S.A.), 11, 1 (1983).] In addition, the use of urea to dissociate complex molecules also has been reported. [Schlecht, S. and Bhatnagar, N., *Zentral Bakteriol Mikrobial Hyg.* (Germany, West) 251(2), 196 (1981); Lehrer, S. B., et al., *Journal of Immunology* (U.S.A.) 114(1), 34 (1975); Dalen, A. B., *Acta Path. Microbiol. Scan.* Section B (Denmark), 83, 561 (1975); Helting, T. B. and Blackkolb, F., "An effective procedure for preparing extracted protected antigen from *Bordetella pertussis*", in *Third International Symposium on Pertussis*, National Institutes of Health, Part 6, pp 331-337 (1978). The use of urea in combination with DEAE-Sephadex chromatography [Kita, E., et al., *Microb. Immunol.*, 27, 7 (1983)] and the use of urea with SDS-polyacrylamide gel electrophoresis [Kew, O. M., et al., *Journal of Virology*, 33, 256 (1980)] are known. However, the process of the sedimenting a protein aggregate through dissociating solutions of varying concentration to solubilize, purify and characterize a protein was not known and is novel.

Therefore, it is an object of this invention to provide a process for solubilizing and purifying protein molecules that are present in cell extracts as insoluble aggregates. More especially, it is an object of this invention to provide a process for producing a relatively pure, if not pure, soluble protein from an insoluble aggregate.

In particular, it is a further object of this invention to provide a process to solubilize, partially purify and characterize proteins from insoluble aggregates in a single step.

Still further, it is an object of this invention to provide compositions of matter such as vaccines comprising one or more proteins which heretofore existed as insoluble protein aggregates.

SUMMARY OF THE INVENTION

The novel process of this invention comprises layering protein aggregates onto a step gradient of two or more varying concentrations of a solution of a dissociating compound, centrifuging the gradient and then fractionating the resulting gradient to locate the solubilized protein of choice. The novel process of this invention identifies a concentration or concentrations of a solution of a dissociating compound which can then be employed to solubilize protein from aggregates without the subsequent use of a step gradient.

Proteins which have been solubilized and purified from insoluble protein aggregates according to this invention are employed in a conventional manner to produce vaccines and other compositions of matter comprising said proteins.

DETAILED DESCRIPTION OF THE INVENTION

Figure 1:
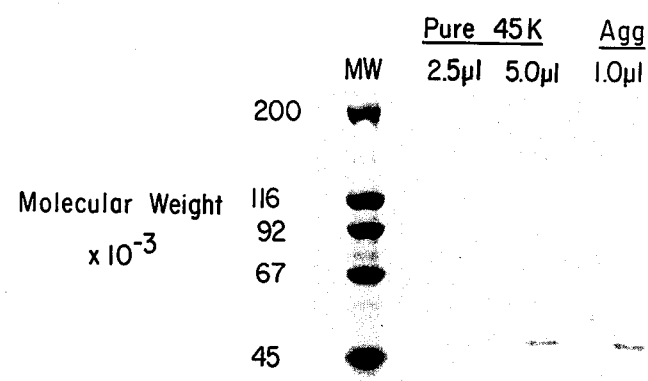

The novel process of this invention has, as its essential attribute, the capacity to solubilize and partially purify protein aggregate components during centrifugation as well as characterize the solubility of the protein aggregate. To accomplish solubilization and simultaneously sediment a protein aggregate through a density step gradient, an urea step gradient is employed herein.

The use of urea in a step gradient provides a combined density and dissociating gradient which is a novel system. The sedimentation and dissociation properties of protein aggregates are utilized to fractionate and thereby partially purify component proteins of such aggregates. The use of guanidine HCl or sodium dodecyl sulphate (SDS) is not an acceptable means of solubilization for certain proteins such as those to be employed as injectables since guanidine HCl may be deleterious to the immunogenicity of the protein and SDS binds tenaciously to proteins. Urea does not exhibit the problems which the use of guanidine HCl and SDS produce and, additionally, urea can be quantitatively removed by dialysis after centrifugation and fractionation.

According to the process of this invention, urea solutions of two or more varying concentrations in a suitable buffer are layered, one on top of the other, in descending concentration in a centrifuge tube. This layering results in the formation of a step gradient. Protein aggregates, suspended in a suitable buffer such as phosphate buffered saline (PBS), are layered on top of the gradient and the gradient is centrifuged. During centrifugation, the aggregates sediment through the urea until an urea concentration is reached which solubilizes the aggregate.

The novel features of the present invention and, more particularly, the novel urea step gradient, perform numerous functions in solubilizing and partially purifying proteins of aggregates. The lower concentrations of urea (i.e. the upper part of the gradient) aid in the removal of non-specifically bound contaminating proteins. The urea solubilized protein remains at the concentration of urea where it is solubilized. Additionally, contaminating components which are insoluble in all urea concentrations employed pellet to the bottom of the centrifuge tube. Furthermore, once the concentration of urea capable of solubilizing the protein of interest is determined by use of the step gradient, direct solubilization without use of the step gradient using the determined urea concentration can be effected, followed by centrifugation to pellet insoluble matter not of interest.

The present invention describes by way of examples the use of this novel process to purify and solubilize recombinant glycoprotein D of Herpes simplex virus Type 1 from aggregates of a total cell extract of *Escherichia coli*. By way of example and not of limitation, the process of the present invention can be applied to protein aggregates of Hepatitis B surface antigens, poliovirus proteins and growth hormone aggregates. Any such variations necessary for the process of this invention to be employed in the purification of a particular protein of an aggregate are, with the disclosure contained herein, within the knowledge of those skilled in the art. The process, however, can be varied to purify different aggregate proteins of similar properties by varying the urea concentrations, pH, salt and ionic concentrations of the buffers and centrifugation conditions that are employed without departing from the scope of the present invention with the proviso that the aggregates must be soluble in at least high molar urea for use of the urea step gradient. Other step gradients such as guanidine HCl can be employed where suitable without departing from the scope of this invention. The centrifugation speed used will depend upon the sedimentation rate of the aggregate as well as the size of the aggregate. Determination of the appropriate centrifugation speed is within the knowledge of those skilled in the art.

In one embodiment of the present invention, the urea step gradient comprises urea concentrations of 7M, 6M, 5M, 4M and 3M. In another embodiment, the urea step gradient comprises urea concentrations of 8M, 7M, 6M, 5M and 4M. In such embodiments the gradient can be centrifuged at about 113,000 xg($r_{max}$) at a temperature of about 4° C. to about 15° C. for about one hour.

In a preferred embodiment of the present invention, the urea concentrations are prepared in buffer comprising 50 mM TRIS(tris(hydroxymethyl)aminomethane), 1 mM EDTA(ethylenediaminetetraacetic acid) and 1 mM DTT(1,4-dithiothreitol), pH 9.0. The protein aggregates of such preferred embodiment are suspended in PBS comprising 0.8 mM sodium phosphate, dibasic, 2.3 mM potassium phosphate, monobasic and 0.15M sodium chloride. The urea concentrations employed in said preferred embodiment are 7M, 6M, 5M, 4M and 3M and the gradient with protein aggregate is centrifuged for about 45 minutes at about 113,000 xg($r_{max}$) at about 10° C.

Following centrifugation of the step gradient, the gradient is fractionated. One such method of fractionation is to puncture the gradient tube at the bottom and to the side of the pellet. Then fractions are collected from the bottom of the tube.

The fractions collected as described above can then be assayed for detection of the protein of interest. For example, samples from the fractions can be assayed by SDS-polyacrylamide gel electrophoresis or other means well known to those skilled in the art. In this manner, the fractions that contain the protein of interest can be ascertained.

The protein contained in the fractions, as determined above, can then be subjected to further purification and/or concentration as needed using techniques that are well known to those skilled in the art. Such techniques include ion exchange chromatography, dialysis and ultra filtration.

Compositions of matter such as vaccines may then be produced according to conventional methods employing proteins which have been solubilized and purified according to the process of this invention. For example, the proteins may be bound to aluminum hydroxide, aluminum phosphate or other pharmaceutically acceptable adjuvant or carrier.

The above prepared vaccines are then employed in a conventional manner to vaccinate against the respective pathogen with the determination of unit doses well known to those skilled in the art. Protection may be elicited after a single dose of vaccine, or may require several booster doses. Vaccine compositions may include, in addition to the protein or proteins, immunologically acceptable diluents and carriers as well as commonly employed adjuvants such as alum, Freund's Complete Adjuvant, saponin, and the like. The vaccine compositions of the present invention can be administered alone or, where immunologically acceptable, in combination with other vaccines.

The process of this invention as applied to the purification of recombinant glycoprotein D-1(gD-1) from a strain of *Escherichia coli* (NF 1829) containing a recombinant plasmid coding for a major portion of gD-1 (pEH 102) is described below. The strain of *Escherichia coli* (NF 1829) containing the recombinant plasmid pEH 102 as well as the glycoprotein D-1 produced thereby is disclosed in the U.S. patent application of Roger J. Watson, John H. Weis and Lynn W. Enquist, Ser. No. 706,538 The recombinant gD-1 protein that is produced thereby is approximately 45K in size (i.e. a molecular weight of approximately 45,000). Therefore, the recombinant gD-1 protein will be referred to hereinafter as 45K or 45K protein. The description of the process as applied to the purification of the 45K protein is provided by way of example and should not be construed to limit this invention in any way to the specific purification process described hereinafter.

EXAMPLE 1

Purification of 45K Protein Obtained From a Portion of a 10 Liter Batch Fermentation of *Escherichia coli* NF1829 (pEH 102) Strain Cell Lysis and Initial Aggregate Purification A 38.2 g (wet weight) portion of a pellet of bacterial cells recovered from the fermentation of NF1829 (pEH 102) strain was resuspended to a total volume of 180 ml in a bacterial cell extraction buffer comprising 20 mM sodium/potassium phosphate, 10% glycerol, 0.5% NP40 (Nonidet P-40, Bethesda Research Laboratories) and 1.0 mM EDTA. The mixture was incubated for about 30 minutes at 4° C. with occasional mixing. Then, 36.0 mg of lysozyme were added to the bacterial cell suspension and the suspension was mixed occasionally while incubating at 4° C. for one hour. A 450 mg amount of Z3-14 powder (Zwittergent 3-14, Calbiochem-Behring Corporation) was added to the above suspension with mixing. Then, the suspension was allowed to incubate at 4° C. with occasional mixing for approximately 30 minutes resulting in a dramatic increase in viscosity. The bacterial lysate was sonicated vigorously for 2 minutes, in one minute bursts with a Heat Systems W-375 sonicator (Ultrasonics Inc.), then centrifuged at 65 xg($r_{max}$) (500 rpm in 259 rotor in a PR-6000 centrifuge (International Equipment Co.)), for 5 minutes, at 4° C. The viscous foam on the top of the supernatant was removed and the supernatant fluid was transferred into SW27, polylallomer 1"×3½" centrifuge tubes (Beckman Instruments Inc.) each containing 3.0 ml of 40% w/v sucrose. The tubes were balanced with bacterial cell extraction buffer, placed in a SW27 rotor and centrifuged at 4° C. for one hour at 113,000 xg($r_{max}$) (25,000 rpm) in a L2-65 ultracentrifuge (Beckman Instruments, Inc.) The supernatant fractions (including sucrose) were collected and stored at −70° C. The residual pellets were resuspended in PBS (0.8 mM sodium phosphate, dibasic, 2.3 mM potassium phosphate, monobasic and 0.15M sodium chloride), sonicated as described hereinabove, then stored at −70° C.

Further purification of the insoluble 45K protein was obtained by thawing the centrifuge tubes containing the resuspended pellets followed by the addition of 250 mg of Z3-14 powder per tube. The contents of the tubes were swirled and sonicated briefly (15–30 seconds) with a Heat Systems standard microtip, then brought to a volume of 50 ml with bacterial cell extraction buffer and swirled again. Equal volumes of the resuspended pellet mixture were distributed among six SW27 centrifuge tubes, each containing 10 ml of freshly prepared 40% sucrose (w/v) in sterile filtered sodium/potassium phosphate buffered saline as described above containing 1 mM EDTA (PBS-EDTA). The tubes were filled with bacterial cell extraction buffer and centrifuged at 113,000 xg($r_{max}$) (25,000 rpm) for one hour at 4° C. in a L2-65 ultracentrifuge. The supernatant and sucrose cuts from each tube were collected and pooled separately leaving the aggregates which had pelleted. The aggregates were resuspended in sterile filtered PBS-EDTA and pooled. The tubes were rinsed with additional buffer and the washes were added to the pooled aggregates which were sonicated for 60 seconds as hereinbefore described. The suspension was then adjusted to a volume of 50.0 ml with sterile filtered PBS-EDTA. This suspension was then stored at 4° C.

Preparation of Urea Step Gradients

A stock solution of 8M urea was prepared by dissolving 240.24 g of urea in about 400 ml of distilled water containing 3.0285 g of tris(hydroxymethyl)aminomethane (TRIS), 146.1 mg of ethylenediaminetetraacetic acid (EDTA) and 77.1 mg of 1,4-dithiothreitol (DTT). The solution was adjusted to pH 9.0 with hydrochloric acid, the volume was brought to 500 ml with distilled water and the solution was filtered through a Nalgene ® 0.2 μm filter (Nalge Co., Division of Sybron Corp., Rochester, NY 14602). The resulting solution (Buffer A) comprises 8M urea, 50 mM TRIS HCl, 1 mM EDTA and 1 mM DTT.

A stock buffered solution without urea (Buffer B) was also prepared in the manner described above comprising 50 mM TRIS, 1 mM EDTA and 1 mM DTT, adjusted to pH 9.0 with hydrochloric acid.

The 48 ml volumes of urea solutions shown in Table I below were prepared utilizing the stock solutions hereinabove described.

TABLE I

| Preparation of Urea Step Gradient Solutions | | |
|---|---|---|
| Molar Concentration of Urea | Volume of Buffer A (ml) | Volume of Buffer B (ml) |
| 8 M | 48.0 | 0.0 |
| 7 M | 42.0 | 6.0 |
| 6 M | 36.0 | 12.0 |
| 5 M | 30.0 | 18.0 |
| 4 M | 24.0 | 24.0 |
| 3 M | 18.0 | 30.0 |

To a series of six SW27 centrifuge tubes was added, layered one over another in descending concentration 6.0 ml of each of the following urea concentrations: 7M, 6M, 5M, 4M and 3M.

Sample Preparation

An 18.0 ml amount of the preceding 45K aggregate solution (50.0 ml) was combined and mixed with 18.0 ml of Buffer B. The 3M layer of the step gradient was then overlaid with 6.0 ml of the prepared sample.

Centrifugation and Fractionation of the Urea Step Gradient

The gradient tubes were placed in a SW27 rotor and centrifuged at about 10° C. and about 113,000 xg($r_{max}$) (25,000 rpm) in a L2-65 ultracentrifuge for about 45 minutes. Gradient fractions were collected from the bottom of the tubes through a needle puncture to the side of the residual pellet. The individual fractions of the 7M, 6M, 5M, 4M and 3M concentrations were collected in separate centrifuge tubes which were labeled according to the molar concentration of urea in the fraction. A yellow colored band which was evident at the interface between fractions aided in the collection. The fraction collection was also aided by the application of air pressure to the top surface of the liquid in the tube. This was accomplished by fitting an air tight stopper to the top of the tube. The stopper was fitted from the top with an 18 gauge syringe needle inserted through the center and just protruding through the stopper bottom. The needle was connected to a 50 ml syringe with a length of small bore pressure tubing.

When the syringe plunger was depressed, compressed air was directed against the top surface of the liquid and thereby allowed controlled collection of the fractions.

The urea gradient fractions of one of the gradients, collected as described above, were subjected to sodium dodecyl sulphate polyacrylamide gel electrophoresis (SDS-PAGE) in a Bio-Rad Protean TM dual slab cell apparatus (Bio-Rad, Inc., 2200 Wright Ave., Richmond, CA 94804) for 16–18 h at 38 V by using a discontinuous buffer system containing a linear 5–20% (w/v) polyacrylamide gradient according to the procedure of Laemmli, U. L., *Nature (London)*, 227; 680 (1970). The gel was stained in a solution containing 0.5% (w/v) coomassie blue—R250 (Bio-Rad) in 50% (v/v) methanol and 7% acetic acid. Excess dye was removed by washing in 5% methanol and 7% acetic acid. Photographs were taken of wet gels after removal of unbound dye. The gel showed the urea solubilized protein was present in the 7M, 6M, 5M and 4M fractions. Then, the 7M, 6M, 5M and 4M urea fractions (total volume of 24 ml) from each of the six gradients were pooled to give 144 ml.

Ion Exchange Chromatography

The pooled fractions (144 ml) containing the soluble 45K protein were mixed with 45 ml of DEAE-Sephacel beads (Pharmacia Fine Chemicals AB, Uppsala, Sweden) which had been previously equilibrated with 0.5M sodium chloride in Buffer A followed by Buffer A without sodium chloride. The beads were reacted with the pooled mixture on a rotating shaker at 4° C. for 48 hours.

Then, the 45K protein solution and beads were loaded slowly into a 48 ml Econo-Column (1.5 cm×30 cm) from Bio-Rad Laboratories, Richmond, CA 94804. The column was then washed with 50 ml of Buffer A and the collection of 4.0 ml fractions of eluate was started. Elution of the protein was then begun by running Buffer A containing 0.5M sodium chloride through the column. The collection of 4.0 ml fractions was continued throughout, monitoring the fractions by SDS-PAGE gel electrophoresis for the presence of 45K protein.

The contents of eluate fractions 11–34 were dialyzed versus a buffer made up of sodium phosphate, dibasic 0.83 g/L, potassium phosphate, monobasic 0.113 g/L, sodium chloride 8.50 g/L and 2% sodium thimerosal. A quantitative protein determination was performed on the dialyzed fractions using a modification of the Lowry protein assay as reported by Sidney P. Colowich and Nathan O. Kaplan in *Methods in Enzymology*, Vol. III, (Academic Press, Inc., 1957) p. 447.

Additionally, fractions 39–50 were individually assayed by electrophoresis on a 5–20% SDS-PAGE gel as hereinbefore described. The results of the protein determinations and the electrophoreses indicated that 45K protein was slowly eluting from the column in the presence of 0.5M sodium chloride.

In order to elute the remaining column bound 45K protein from the DEAE-Sephacel beads, a solution of Buffer A containing 1M sodium chloride was prepared. This solution was passed through the column and the collection of 4.0 ml fractions of eluate was continued (encompassing fractions 51–79). Analysis of the individual fractions by SDS-PAGE as hereinabove described showed that the elution of the protein was essentially complete in the final eluate.

Fractions 51–58 and 59–66 were pooled separately and dialyzed as hereinbefore described to give 33.0 ml and 32.0 ml respectively. The total protein content of the pooled fractions was determined by the Lowry procedure to be 10.82 mg and 11.64 mg respectively. The two volumes were combined (65 ml) and concentrated to 40.0 ml in a 50 ml Amicon ® filtration unit (Amicon Corporation, Danvers, MA 01923) fitted with a PM-10 membrane using 40 psi of nitrogen gas. The concentrated filtrate was assayed by the Lowry protein assay and showed that 73.5% (0.4129 µg/ml) of the total protein loaded onto the column was recovered.

The 45K protein concentrate was then assayed by gel electrophoresis on a 5–20% SDS-PAGE gel as described above by applying 2.5 and 5.0 microliter aliquots of the concentrate to the gel and comparing the protein with high molecular weight protein markers (HMW) and a 1.0 microliter aliquot of the 45K pooled aggregate prior to centrifugation through the urea step gradient. See FIG. 1 below.

FIG. 1 is a photograph of SDS-PAGE showing the location of: the HMW markers at gel slot 2; the 2.5 microliter aliquot of the purified 45K concentrate at gel slot 4; the 5.0 microliter aliquot of the purified 45K concentrate at gel slot 6; and the one microliter aliquot of the 45K pooled aggregate at gel slot 8.

Scanning densitometric reflectance analysis performed on the "wet gel" using a CAMAG densitometer TLC scanner (CAMAG, Muttenz, Switzerland) at a wavelength of 610 nm indicated that from 83.4–100% of the total protein recovered from the column is the 45K protein.

In Vivo Testing of Soluble 45K

The soluble 45K protein produced according to the process of this invention provides protection of mice against footpad challenge with Herpes simplex virus type 2. A test designed to determine the protection of mice against footpad challenge with Herpes simplex virus Type 2 (HSV-2) after immunization with gD-related recombinant proteins uses female, Balb/c mice. Groups of six to ten mice were used for each vaccine tested, with 10 unimmunized mice used as a control. The vaccines tested were: 45K aggregate in PBS; soluble 45K in PBS; soluble 45K bound to aluminum hydroxide; and native gD-1 (native glycoprotein D from HSV-1 infected cells) bound to aluminum hydroxide. Also evaluated separately were the PBS and aluminum hydroxide vehicles.

Mice were inoculated intramuscularly (first immunization) with 0.2 ml of vaccine or vehicle on day zero. On day 21 after the first immunization the animals received a second intramuscular inoculation (imumunization) with 0.2 ml of the vaccine or vehicle. Recombinant proteins were given at a total dose of 100 µg/mouse (50 µg/mouse/immunization) and native gD-1 at a total dose of 6 µg/mouse (3 µg/mouse/immunization). On day 28 after the first immunization, mice were bled by retro-orbital bleeding. Then, on day 30, mice were inoculated with HSV-2 strain 186, the challenge virus. The dose of challenge virus inoculated per mouse was calculated to have $\geq 32$ $PD_{50}$. One $PD_{50}$ is the dose of the virus that causes paralysis in 50% of the mice inoculated. The challenge dose was administered by inoculating 0.03 ml of the virus into the right hind leg footpad of each mouse. An observation period of 50 days from the virus challenge was then begun.

The results of the in vivo test appear in Table II below. Immunization with soluble 45K-Al(OH)$_3$ afforded all mice protection from paralysis and/or death.

TABLE II

Protection of Mice Against Footpad Challenge With HSV-2 After Immunization With gD-Related Recombinant Proteins

| Vaccine | No. With Paralysis | No. Dead | Dead/ Paralyzed* | % Dead or Paralyzed | Serum Neutralization Geometric Mean Titers Type 1 | Type 2 |
|---|---|---|---|---|---|---|
| 45K - Agg PBS | 0/6 | 3/6 | 0/6 | 50 | 28 | 12 |
| 45K - Sol. PBS | 1/10 | 3/10 | 0/1 | 40 | ≧104 | 37 |
| 45K - Sol. Al(OH)$_3$ | 0/10 | 0/10 | 0/0 | 0 | ≧256 | 91 |
| Native gD-1 Al(OH)$_3$ | 1/10 | 1/10 | 0/1 | 20 | ≧256 | 137 |
| PBS | 10/10 | 6/10 | 6/10 | 100 | <6 | <6 |
| Al(OH)$_3$ | 10/10 | 2/10 | 2/10 | 100 | <6 | <6 |
| Unimmunized | 7/10 | 7/10 | 4/7 | 100 | ND | ND |

Mice received ≧32 PD$_{50}$ of HSV-2-186 in 0.03 ml via right footpad (1.8 × 10$^8$ PFU).
Observation period = 50 days
Recombinant proteins were given at a total dose of 100 μg/mouse, native gD-1 at a total dose of 6 μg/mouse.
*Represents the number of paralyzed mice that died, over the total number of paralyzed mice.
ND = Not done.

In Vitro Testing of Soluble 45K

The soluble 45K was tested in vitro according to a microneutralization assay which is described below. Ninety-six well tissue culture plates were seeded with Baby Hamster Kidney (BHK) cells at a density of 4.5×10$^4$ cells per well in Eagle's minimal essential medium (EMEM) containing 5% fetal calf serum (FCS) and 0.1% gentamycin. The plates then were incubated at 37° C. in a 5% CO$_2$ incubator until the cells grew to confluency. Then, serial two-fold dilutions of control or experimental sera from immunized mice were prepared in 96-well dilution plates (wells G through A) using EMEM as diluent. Row H received 15 μl of diluent per ml and represented serum-free controls. Row G was used to prepare the initial 30 μl of a 1:3 dilution of serum samples. Serial two-fold dilutions of serum were prepared from row G to row A. Final dilutions ranged from 1:6 to 1:384.

Stocks of Herpes simplex virus Type 1 (HSV-1) strain McIntyre or Type 2 (HSV-2) strain savage were diluted into EMEM containing 30% heat inactivated (56° C., 30 min.) FCS and 10% guinea pig complement. Final virus dilutions were prepared so that 15 μl contained 60 plaque forming units (PFU) of virus. Fifteen μl aliquots of the appropriate virus type and dilution were added to each of the 15 μl serum dilutions in the 96 well dilution plates (see above). The plates were incubated at 37° C. for 60 min, then 25 μl aliquots were removed from each well and transferred to the corresponding wells in freshly evaluated 96-well tissue culture plates containing confluent monolayers of BHK cells. Cell cultures were incubated for 90 min. at 37° C., then 200 μl of EMEM containing 1.5% methylcellulose, 5% FCS, and 0.1% gentamycin was added to each well. Plates were incubated at 37° C. overnight or until virus plaques developed as determined by light microscopy. Plaques were counted and neutralizing titers were expressed as the highest serum dilution resulting in 50% plaque reduction.

The results of the microneutralization assay are shown in Table II above as serum neutralization. The sera from mice immunized with soluble 45K exhibit high serum neutralization. The serum from mice immunized with soluble 45K-Al(OH)$_3$ exhibits serum neutralization comparable to serum from mice immunized with native gD-1.

EXAMPLE 2

Direct Solubilization and Purification of 45K Protein Obtained From a Portion of a 10 Liter Batch Fermentation of *Escherichia coli* NF1829 (pEH 102) Strain The novel process as described in Example 1 above showed that the 45K protein was soluble from the aggregate in 6M urea. Based on the solubility characterization of the 45K protein, the following described large scale purification process was employed wherein 6M urea was used.

Cell Lysis and Initial Aggregate Purification

A 72.55 g (wet weight) portion of bacterial cells recovered from the fermentation of NF1829 (pEH 102) strain was resuspended in bacterial cell extraction buffer as described in Example 1 to a total volume of 325 ml. The suspension was mixed well and then 6 ml of a 12 mg/ml lysozyme solution (72 mg) were added. The suspension with the lysozyme was incubated on a rotator at 4° C. for 1 hour. Following the incubation, 18.4 ml of 10% Z3-14 (Zwittergent 3-14, Calbiochem-Behring Corporation) was added and mixed well and the incubation was continued on a rotator at 4° C. for 15 minutes. Thirty (30) ml aliquots were sonicated as described in Example 1 to reduce viscosity of the lysate. Following sonication, the 30 ml aliquots were layered onto 6 ml of 40% (w/v) sucrose and centrifuged at 113,000×g (r$_{max}$) (25,000 rpm) in a SW27 rotor in a L2-65 ultracentrifuge (Beckman Instruments, Inc.) at 4° C. for 45 minutes. The supernatant and sucrose fractions were discarded and the pellets were resuspended by sonication in a total volume of 240 ml of PBS. Then, 0.24 ml of 0.1M phenylmethylsulfonyl fluoride (PMSF) was added to the suspension and the suspension was incubated on a rotator at 4° C. overnight.

Following overnight incubation, the suspension was centrifuged through sucrose again, as described above. Once again, the supernatant and sucrose fractions were discarded and the pellets were resuspended by sonication (45-60 seconds) in PBS.

Similarly, 72.41 g and 72.26 g portions of bacterial cells from the same fermentation were treated and the resuspended pellets, following centrifugation through sucrose, were pooled with the above suspension to yield a final volume of 250 ml of 45K protein aggregate suspension in PBS. The suspension was divided into two (2) 125 ml portions and stored frozen at −70° C.

Urea Solubilization and Centrifugation

The stored 45K aggregate suspension was thawed and 44.4 ml aliquots of one (1) 125 ml portions were mixed well with 177.6 ml of Buffer A as described in Example 1. The mixture was distributed into 6 SW27 centrifuge tubes (37 ml per tube) and centrifuged at about 113,000xg ($r_{max}$) as described above. The supernatants were pooled and stored at −70° C. One pellet was resuspended in PBS for assay by SDS-PAGE as described in Example 1.

The remaining 125 ml portion of the thawed 45K aggregate suspension was diluted 1:2 with PBS. Then 52 ml of the suspension was mixed with Buffer A as described above. The remaining 198 ml of suspension was subjected to urea step gradient centrifugation (8M-2M gradient) as described in Example 1. The urea step gradient fractions containing the 45K protein in solution were re-centrifuged at about 113,000 xg ($r_{max}$) and about 10° C. and the supernatants of all fractions were pooled, resulting in a total volume of 400 ml.

Ion Exchange Chromatography

All urea solutions containing the 45K protein were pooled and the volume was adjusted to 1500 ml with Buffer A. Six aliquots of 225 ml each were mixed with 33.3 ml of a 77.8% slurry of DEAE-Sephacel beads equilibrated as described in Example 1. The remaining solution of 45K protein (150 ml) was mixed with 25.9 ml of the same DEAE-Sephacel slurry. The solutions plus beads then were incubated on a rotator at room temperature for 1 hour.

The beads were pelleted twice at low speed (600 rpm) for 5 minutes in a PR-6000 centrifuge (International Equipment Co.). The protein was eluted from the beads as follows. With approximately 100 ml of beads containing bound protein in two (2) 250 ml centrifuge tubes, 100 ml of an elution buffer was added. The suspension was incubated for 8 minutes at room temperature and then centrifuged at 600 rpm for 5 minutes at 10° C. The supernatant was removed and stored at −70° C. and the next elution buffer was mixed with the beads. Then, the process was repeated saving the supernatants after each elution.

Using the above procedure, Buffer A containing the following NaCl concentrations was employed in the order as indicated below: (1) 0M NaCl, (2) 0M NaCl, (3) 0.2M NaCl, (4) 0.4M NaCl, (5) 0.6M NaCl, (6) 0.8M NaCl, (7) 1.0M NaCl, (8) 1.0M NaCl. The last elution buffer (8) was incubated overnight before centrifugation.

To increase the recovery of 45K protein, the remaining protein in the supernatant following initial reaction with the DEAE-Sephacel beads can be mixed again with the beads and subjected to elution. Accordingly, the beads were reacted for 2 hours at room temperature on a rotator with the supernatant containing residual 45K protein. The beads were pelleted as described above, washed three times with Buffer A and then eluted six times as described above but using 10 mM NaCl buffer for the first three elutions and 0.8M NaCl buffer for the last three elutions. Then, a final elution was performed by adding 1.0M NaCl, incubating overnight on a rotator at room temperature and then pelleting the beads.

The 45K protein solution eluted from the beads was dialysed against sterile, pyrogen free PBS, pH 7.0 with three changes which reduced the urea concentration of the solution to approximately 0.00792M. It should be noted, however, that the concentration of the 45K protein may be too great to maintain the protein in solution following dialysis. To eliminate this problem the solution can be diluted before dialysis. If precipitation occurs during dialysis, the precipitate can be redissolved in Buffer A (which also results in a dilution) and dialysed again. For the 45K protein, a concentration greater than about 4 mg/ml was found to precipitate upo the removal of urea.

The protein solution can then be concentrated to the limit of solubility using techniques known to those skilled in the art such as ultrafiltration.

Figure 2:
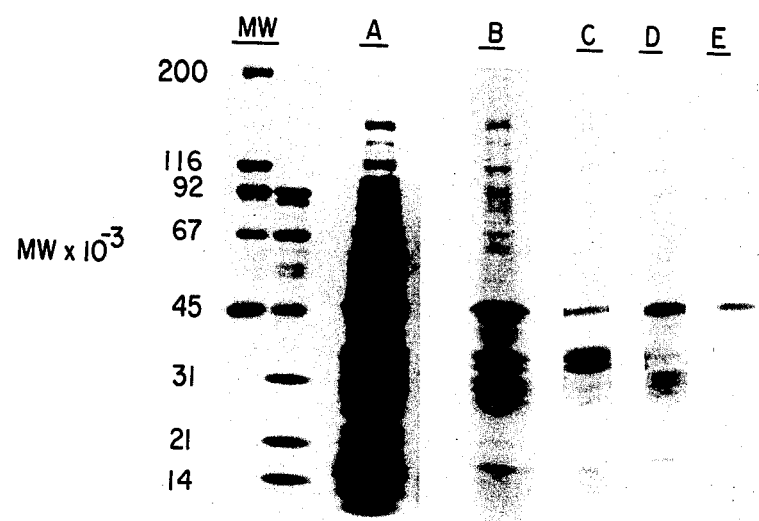

FIG. 2 below shows the results of SDS-PAGE, as described in Example 1, on (A) total cell extract, (B) 45K aggregate, (C) a sample of the concentrated pellet after urea solubilization of aggregates and ultracentrifugation, (D) the supernatant fraction after urea solubilization of aggregates and centrifugation, and (E) soluble 45K after DEAE-Sephacel elution. Also included in FIG. 2 are molecular weight markers (MW) and the numbers to the left in the figure correspond to the molecular weight $\times 10^{-3}$.

I claim:

1. A process for solubilizing, purifying and characterizing a protein from a protein aggregate or complex which comprises layering a suspension of the protein aggregate or complex onto an urea step gradient of two or more varying concentrations; centrifuging the urea step gradient with the protein aggregate or complex layered thereon; and identifying the urea concentration step or steps at which the protein is in solution.

2. The process as recited in claim 1 wherein identifying the concentration step or steps comprises fractionating the urea step gradient after centrifugation and electrophoresing the fractions or samples of the fractions.

3. The process as recited in claim 1 or 2 which further comprises chromatographing the soluble protein.

4. The process as recited in claim 3 which further comprises dialyzing the chromatographed soluble protein and concentrating the protein in solution.

5. The process as recited in claim 4 wherein the urea step gradient comprises about 7M, 6M, 5M, 4M and 3M urea.

6. The process as recited in claim 1 which further comprises solubilizing the protein aggregate or complex in the concentration identified to contain the protein in solution and centrifuging the solution to remove insoluble matter.

7. The process as recited in claim 6 which further comprises chromatographing the soluble protein.

8. The process as recited in claim 6 which further comprises chromatographing the soluble protein; dialyzing the chromatographed protein; and concentrating the protein in solution.

9. The process as recited in claim 1, or 6 wherein the protein comprises at least part of glycoprotein D-1 of Herpes simplex virus Type I and the protein aggregate or complex is the aggregate or complex produced by *Escherichia coli* NF1829 (pEH 102) strain.

10. The process as recited in claim 4 wherein the protein comprises at least part of glycoprotein D-1 of Herpes simplex virus Type I and the protein aggregate or complex is the aggregate or complex produced by *Escherichia coli* NF1829 (pEH 102) strain.

11. The process as recited in claim 8 wherein the protein comprises at least part of glycoprotein D-1 of Herpes simplex virus Type I and the protein aggregate or complex is the aggregate or complex produced by *Escherichia coli* NF1829 (pEH 102) strain.

12. A composition of matter comprising one or more proteins purified according to the process of claim 1.

13. A composition of matter comprising one or more proteins purified according to the process of claim 6.

14. A composition of matter comprising one or more proteins purified according to the process of claim 4.

15. A composition of matter comprising one or more proteins purified according to the process of claim 8.

16. A vaccine composition comprising one or more proteins purified according to the process of claim 5.

17. A vaccine composition comprising one or more proteins purified according to the process of claim 8.

18. A vaccine composition comprising one or more proteins purified according to the process of claim 9 and a pharmaceutically acceptable adjuvant, diluent or carrier.

19. A vaccine composition comprising one or more proteins purified according to the process of claim 10 and a pharmaceutically acceptable adjuvant, diluent or carrier.

20. A vaccine composition comprising one or more proteins purified according to the process of claim 11 and a pharmaceutically acceptable adjuvant, diluent or carrier.

* * * * *